(12) United States Patent
Rabbani et al.

(10) Patent No.: US 7,316,900 B2
(45) Date of Patent: Jan. 8, 2008

(54) METHYLATED NUCLEOTIDE REGULATION OF GENE EXPRESSION

(75) Inventors: Shafaat A. Rabbani, Westmount (CA); Clarke Slemon, Portland (CA)

(73) Assignee: Quebepharma Recherche, Inc., Montreal, Quebec (CA)

( * ) Notice: Subject to any disclaimer, the term of this patent is extended or adjusted under 35 U.S.C. 154(b) by 389 days.

(21) Appl. No.: 10/332,542

(22) PCT Filed: Jul. 13, 2001

(86) PCT No.: PCT/CA01/01023

§ 371 (c)(1), (2), (4) Date: Jul. 31, 2003

(87) PCT Pub. No.: WO02/06462

PCT Pub. Date: Jan. 24, 2002

(65) Prior Publication Data

US 2004/0053259 A1 Mar. 18, 2004

(30) Foreign Application Priority Data

Jul. 13, 2000 (CA) .................................. 2312051

(51) Int. Cl.
*C12Q 1/68* (2006.01)
*C12P 19/34* (2006.01)
*C07H 21/00* (2006.01)
*C07H 21/02* (2006.01)
*C07H 21/04* (2006.01)

(52) U.S. Cl. .................. 435/6; 435/91.1; 435/91.2; 435/91.5; 536/23.1; 536/24.1; 536/24.31; 536/24.33

(58) Field of Classification Search .............. 435/455, 435/458, 6, 91.1, 91.3, 91.2, 325, 252.3, 435/91.5; 536/23.1, 24.1, 24.3, 24.31, 24.33, 536/24.5
See application file for complete search history.

(56) References Cited

U.S. PATENT DOCUMENTS

| 5,552,390 | A | 9/1996 | Iversen et al. | |
|---|---|---|---|---|
| 5,840,497 | A | 11/1998 | Holiday | |
| 5,874,416 | A | 2/1999 | Sheikhnejad | |
| 6,812,339 | B1 * | 11/2004 | Venter et al. | 536/24.31 |
| 6,900,016 | B1 * | 5/2005 | Venter et al. | 435/6 |

FOREIGN PATENT DOCUMENTS

| WO | WO 94/29461 A | 12/1994 |
|---|---|---|
| WO | WO 97/46705 A | 11/1997 |
| WO | WO 99/24560 A | 5/1999 |

OTHER PUBLICATIONS

Chirila, T.V. et al., Biomaterials, vol. 23, pp. 321-342 (2002).*
Opalinska, J.B. et al., Nature Rev., vol. 1, pp. 503-514 (2002).*
A.D. Branch, Trends in Biochem. Sci., vol. 23, pp. 45-50 (1998).*
A. Peracchi, Rev. Med. Virol., vol. 14, pp. 47-64 (2004).*
Agrawal, S. et al., Molecular Med. Today, vol. 6, pp. 72-81 (2000).*
S.T. Crooke, Antisense Res. & Application, Chapter 1, pp. 1-50 ed. S. Crooke, Publ. Springer-Verlag (1998).*
Guo et al. DNA methylation status of uPA promoter directly affects the expression of uPA in human breast cancer cells to alter their invasive potential. Proceedings of the American Association for Cancer Research Annual, vol. 42, Mar. 2001, p. 625-626.
Guo et al. Regulation of DNA methylation in human breast cancer: Effect of urokinase (uPA) production and tumor and tumor invasion. Proceedings of the American Association for Cancer Research Annual, vol. 41, Mar. 2000, p. 79.
Juan et al. Histone deacetylases specifically down-regulate p53-dependent gene activation. J Biol Chem. Jul. 7, 2000;275(27):20436-43.
Phillips (ed). "Methods of Delivery" Section II of *Methods of Enzymology*. vol. 313, p. 287-397, 1999.
Ricco et al. The human urokinase-plasminogen activator gene and its promoter. Nucleic Acids Research 13(8):2759-85, 1985.
Xing et al. Transcriptional regulation of urokinase (uPA) gene expression in breast cancer cells: role of DNA methylation. Int J Cancer. May 5, 1999;81(3):443-50.
Xing et al. Transcriptional regulation of urokinase (uPA) gene expression in hormone dependent malignancies: Potential role of DNA methylation. Proceedings of the American Association for Cancer Research Annual, vol. 39, Mar. 1998, p. 451.
Yao et al. A methylated oligonucleotide inhibits IGF2 expression and enhances survival in a model of hepatocellular carcinoma. J Clin Invest. Jan. 2003;111(2):265-73.

* cited by examiner

*Primary Examiner*—Jane Zara
(74) *Attorney, Agent, or Firm*—Jones Day

(57) ABSTRACT

The present invention provides a method of regulating the expression of the urokinase type plasminogen activator ("uPA") gene in a mammalian cell comprising the steps of: identifying a target nucleotide sequence in a gene of interest, obtaining a methylated antisense oligonucleotide sequence complementary to the target sequence, said oligonucleotide sequence having 5 methylated cytosine in place of unmethylated cytosine in the region complementary to the CpG region in the target nucleotide sequence, and exposing the cell to copies of the oligonucleotide sequence under suitable conditions, such that the oligonucleotide sequence enters the nucleus and interacts with the target sequence to promote methylation of the target nucleotide sequence.

22 Claims, 3 Drawing Sheets

```
       592 ..cggagaatt tacaagcctc tcgattcctc agtccagacg ctgttgggtc cctccgctg gagatcgcgc
LNCaP          ..........  ..........  ..........  ..........  ..........  .........  ........
PC3            ..........  ..........  ..........  ..........  ..........  ....c^m..  ..c^m..c^m
MCF-7          ..........  ..........  ..........  ..........  ..........  .........  ..c^m....
MDA-MB-231     ..........  ..........  ..........  ..........  ..........  .........  ..c^m..c^m 661 ttcccccaaa tctttgtgag cgttgcggaa gcacgcgggg tccgggtcgc tgagcgctgc aagacagggg agggagccgg
               ..........  ..........  ...c^m.....  ..c^m.c^m.  ..c^m.c^m.  ....c^m...  ..........  ....c^m...
               ..........  ..........  ...c^m.....  ..c^m.c^m.  ..c^m.c^m.  ....c^m...  ..........  ....c^m...
               ..........  ..........  ...........  ..........  ..........  ....c^m...  ..........  ..........
               ..........  ..........  ...........  ..........  ..........  ....c^m...  ..........  ..........

741 gcgggagagg gaggggcggc gcggggggcg gccctgatat agagcaggcg ccgcgggtcg cagcacagtc ggagaccgca
               ..........  ..........  ..........  ..........  ..........  .....c^m..  ...c^m....  ........c^m
               ....c^m...  ....c^m.c^m  ..........  ..........  ..........  .....c^m..  ...c^m....  ........c^m
               ..........  ..........  ..........  ..........  ..........  .....c^m..  ..........  ..........
               ..........  ..........  ..........  ..........  ..........  .....c^m..  ..........  ..........

821 gcccggagcc cgggccaggg tccacctgtc cccgcagcgc cggctcgcgc cctcctgccg cagccaccgg t... 891
               ....c^m.c^m  ..........  ..........  ..........  ....c^m....  .c^m..c^m..  ...c^m....  ...c^m....
               ....c^m.c^m  ..........  ..........  ..........  ....c^m....  .c^m..c^m..  ...c^m....  ...c^m....
               ..........  ..........  ..........  ..........  ..........  ..........  ..........  ..........
               ....c^m...  ..........  ..........  ..........  ..........  ..........  ..........  ..........
```

Figure 3

SEQUENCE LISTING

<160> NUMBER OF SEQ ID NOS: 17

<210> SEQ ID NO 1
<211> LENGTH: 18
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n at position 1 is m5c
<220> FEATURE:
<221> NAME/KEY: misc_feature
<222> LOCATION: (16)..(16)
<223> OTHER INFORMATION: n at position 16 is m5c

<400> SEQUENCE: 1
ngaaagcaat aagccngg                                                   18

<210> SEQ ID NO 2
<211> LENGTH: 39
<212> TYPE: DNA
<213> ORGANISM: Homo sapiens
<220> FEATURE:
<221> NAME/KEY: misc_feature
<222> LOCATION: (4)..(4)
<223> OTHER INFORMATION: n at position 4 is m5c
<220> FEATURE:
<221> NAME/KEY: misc_feature
<222> LOCATION: (6)..(6)
<223> OTHER INFORMATION: n at position 6 is m5c
<220> FEATURE:
<221> NAME/KEY: misc_feature -continued

```
<222> LOCATION: (35)..(35)
<223> OTHER INFORMATION: n at position 35 is m5c

<400> SEQUENCE: 2
tgtngngtga tgaagacttc acagctccat ccagngacc                              39

<210> SEQ ID NO 3
<211> LENGTH: 33
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n at position 1 is m5c
<220> FEATURE:
<221> NAME/KEY: misc_feature
<222> LOCATION: (3)..(3)
<223> OTHER INFORMATION: n at position 3 is m5c
<220> FEATURE:
<221> NAME/KEY: misc_feature
<222> LOCATION: (32)..(32)
<223> OTHER INFORMATION: n at position 32 is m5c

<400> SEQUENCE: 3
ngngtgatga agacttcaca gctccatcca gng                                    33

<210> SEQ ID NO 4
<211> LENGTH: 30
<212> TYPE: DNA
<213> ORGANISM: Homo sapiens
<220> FEATURE:
<221> NAME/KEY: misc_feature
<222> LOCATION: (1)..(2)
<223> OTHER INFORMATION: n at position 1 is m5c
<220> FEATURE:
<221> NAME/KEY: misc_feature
<222> LOCATION: (29)..(29)
<223> OTHER INFORMATION: n at position 29 is m5c

<400> SEQUENCE: 4 ngggactcc ttgcactggg gcaggcccng                                         30

<210> SEQ ID NO 5
<211> LENGTH: 33
<212> TYPE: DNA
<213> ORGANISM: Homo sapiens
<220> FEATURE:
<221> NAME/KEY: misc_feature
<222> LOCATION: (2)..(2)
<223> OTHER INFORMATION: n at position 2 is m5c
<220> FEATURE:
<221> NAME/KEY: misc_feature
<222> LOCATION: (19)..(19)
<223> OTHER INFORMATION: n at position 19 is m5c
<220> FEATURE:
<221> NAME/KEY: misc_feature
<222> LOCATION: (29)..(29)
<223> OTHER INFORMATION: n at position 29 is m5c
<220> FEATURE:
<221> NAME/KEY: misc_feature
<222> LOCATION: (31)..(31)
<223> OTHER INFORMATION: n at position 31 is m5c

<400> SEQUENCE: 5
angctgttgg gtcccctcng ctggagatng ngc                                    33

<210> SEQ ID NO 6
<211> LENGTH: 24
<212> TYPE: DNA
<213> ORGANISM: Homo sapiens
<220> FEATURE:
```

```
<221> NAME/KEY: misc_feature
<222> LOCATION: (3)..(3)
<223> OTHER INFORMATION: n at position 3 is m5c
<220> FEATURE:
<221> NAME/KEY: misc_feature
<222> LOCATION: (8)..(8)
<223> OTHER INFORMATION: n at position 8 is m5c
<220> FEATURE:
<221> NAME/KEY: misc_feature
<222> LOCATION: (18)..(18)
<223> OTHER INFORMATION: n at position 8 is m5c

<400> SEQUENCE: 6
agngttgngg aagcacgngg ggtc                                               24

<210> SEQ ID NO 7
<211> LENGTH: 36
<212> TYPE: DNA
<213> ORGANISM: Homo sapiens
<220> FEATURE:
<221> NAME/KEY: misc_feature
<222> LOCATION: (3)..(3)
<223> OTHER INFORMATION: n at position 3 is m5c
<220> FEATURE:
<221> NAME/KEY: misc_feature
<222> LOCATION: (7)..(7)
<223> OTHER INFORMATION: n at position 7 is m5c
<220> FEATURE:
<221> NAME/KEY: misc_feature
<222> LOCATION: (22)..(22)
<223> OTHER INFORMATION: n at position 22 is m5c
<220> FEATURE:
<221> NAME/KEY: misc_feature
<222> LOCATION: (28)..(28)
<223> OTHER INFORMATION: n at position 28 is m5c
<220> FEATURE:
<221> NAME/KEY: misc_feature
<222> LOCATION: (33)..(33)
<223> OTHER INFORMATION: n at position 33 is m5c

<400> SEQUENCE: 7 gcngggngg agagggaggg gnggcgcngg ggnggg                                   36

<210> SEQ ID NO 8
<211> LENGTH: 48
<212> TYPE: DNA
<213> ORGANISM: Homo sapiens
<220> FEATURE:
<221> NAME/KEY: misc_feature
<222> LOCATION: (3)..(3)
<223> OTHER INFORMATION: n at position 3 is m5c
<220> FEATURE:
<221> NAME/KEY: misc_feature
<222> LOCATION: (6)..(6)
<223> OTHER INFORMATION: n at position 6 is m5c
<220> FEATURE:
<221> NAME/KEY: misc_feature
<222> LOCATION: (8)..(8)
<223> OTHER INFORMATION: n at position 8 is m5c
<220> FEATURE:
<221> NAME/KEY: misc_feature
<222> LOCATION: (13)..(13)
<223> OTHER INFORMATION: n at position 13 is m5c
<220> FEATURE:
<221> NAME/KEY: misc_feature
<222> LOCATION: (31)..(31)
<223> OTHER INFORMATION: n at position 31 is m5c
<220> FEATURE:
<221> NAME/KEY: misc_feature
<222> LOCATION: (38)..(38)
<223> OTHER INFORMATION: n at position 38 is m5c
<220> FEATURE:
<221> NAME/KEY: misc_feature
<222> LOCATION: (45)..(45)
<223> OTHER INFORMATION: n at position 45 is m5c
```

<400> SEQUENCE: 8
ggngcngngg gtngcagcac agtcggagac ngcagccngg agccnggg            48

<210> SEQ ID NO 9
<211> LENGTH: 156
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n at position 1 is m5c
<220> FEATURE:
<221> NAME/KEY: misc_feature
<222> LOCATION: (11)..(11)
<223> OTHER INFORMATION: n at position 11 is m5c
<220> FEATURE:
<221> NAME/KEY: misc_feature
<222> LOCATION: (13)..(13)
<223> OTHER INFORMATION: n at position 13 is m5c
<220> FEATURE:
<221> NAME/KEY: misc_feature
<222> LOCATION: (36)..(36)
<223> OTHER INFORMATION: n at position 36 is m5c
<220> FEATURE:
<221> NAME/KEY: misc_feature
<222> LOCATION: (41)..(41)
<223> OTHER INFORMATION: n at position 41 is m5c
<220> FEATURE:
<221> NAME/KEY: misc_feature
<222> LOCATION: (49)..(49)
<223> OTHER INFORMATION: n at position 49 is m5c
<220> FEATURE:
<221> NAME/KEY: misc_feature
<222> LOCATION: (51)..(51)
<223> OTHER INFORMATION: n at position 51 is m5c
<220> FEATURE:
<221> NAME/KEY: misc_feature
<222> LOCATION: (58)..(58)
<223> OTHER INFORMATION: n at position 58 is m5c
<220> FEATURE:
<221> NAME/KEY: misc_feature
<222> LOCATION: (63)..(63)
<223> OTHER INFORMATION: n at position 63 is m5c
<220> FEATURE:
<221> NAME/KEY: misc_feature
<222> LOCATION: (70)..(70)
<223> OTHER INFORMATION: n at position 70 is m5c
<220> FEATURE:
<221> NAME/KEY: misc_feature
<222> LOCATION: (93)..(93)
<223> OTHER INFORMATION: n at position 93 is m5c
<220> FEATURE:
<221> NAME/KEY: misc_feature
<222> LOCATION: (97)..(97)
<223> OTHER INFORMATION: n at position 97 is m5c
<220> FEATURE:
<221> NAME/KEY: misc_feature
<222> LOCATION: (112)..(112)
<223> OTHER INFORMATION: n at position 112 is m5c
<220> FEATURE:
<221> NAME/KEY: misc_feature
<222> LOCATION: (118)..(118)
<223> OTHER INFORMATION: n at position 118 is m5c
<220> FEATURE:
<221> NAME/KEY: misc_feature
<222> LOCATION: (123)..(123)
<223> OTHER INFORMATION: n at position 123 is m5c
<220> FEATURE:
<221> NAME/KEY: misc_feature
<222> LOCATION: (144)..(144)
<223> OTHER INFORMATION: n at position 144 is m5c
<220> FEATURE:
<221> NAME/KEY: misc_feature
<222> LOCATION: (147)..(147)
<223> OTHER INFORMATION: n at position 147 is m5c
<220> FEATURE:

```
<221> NAME/KEY: misc_feature
<222> LOCATION: (149)..(149)
<223> OTHER INFORMATION: n at position 149 is m5c
<220> FEATURE:
<221> NAME/KEY: misc_feature
<222> LOCATION: (154)..(154)
<223> OTHER INFORMATION: n at position 154 is m5c

<400> SEQUENCE: 9
ngctggagat ngngcttccc ccaaatcttt gtgagngttg nggaagcang ngggtcngg      60 gtngctgagn gctgcaagac agggaggga gcngggnggg agagggaggg gnggcgcngg    120
ggngggccct gatatagagc aggngcngng ggtngc                             156

<210> SEQ ID NO 10
<211> LENGTH: 20
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n at position 1 is m5c
<220> FEATURE:
<221> NAME/KEY: misc_feature
<222> LOCATION: (3)..(3)
<223> OTHER INFORMATION: n at position 3 is m5c
<220> FEATURE:
<221> NAME/KEY: misc_feature
<222> LOCATION: (10)..(10)
<223> OTHER INFORMATION: n at position 10 is m5c
<220> FEATURE:
<221> NAME/KEY: misc_feature
<222> LOCATION: (15)..(15)
<223> OTHER INFORMATION: n at position 15 is m5c

<400> SEQUENCE: 10 ngngggtcn gggtngctga                                                 20

<210> SEQ ID NO 11
<211> LENGTH: 18
<212> TYPE: DNA
<213> ORGANISM: Homo sapiens
<220> FEATURE:
<221> NAME/KEY: misc_feature
<222> LOCATION: (4)..(4)
<223> OTHER INFORMATION: n at position 4 is m5c
<220> FEATURE:
<221> NAME/KEY: misc_feature
<222> LOCATION: (7)..(7)
<223> OTHER INFORMATION: n at position 7 is m5c
<220> FEATURE:
<221> NAME/KEY: misc_feature
<222> LOCATION: (10)..(10)
<223> OTHER INFORMATION: n at position 10 is m5c
<220> FEATURE:
<221> NAME/KEY: misc_feature
<222> LOCATION: (15)..(15)
<223> OTHER INFORMATION: n at position 15 is m5c

<400> SEQUENCE: 11
gggnggngcn ggggnggg                                                  18

<210> SEQ ID NO 12
<211> LENGTH: 15
<212> TYPE: DNA
<213> ORGANISM: Homo sapiens
<220> FEATURE:
<221> NAME/KEY: misc_feature
<222> LOCATION: (3)..(3)
<223> OTHER INFORMATION: n at position 3 is m5c
<220> FEATURE:
<221> NAME/KEY: misc_feature
```

```
<222> LOCATION: (6)..(6)
<223> OTHER INFORMATION: n at position 6 is m5c
<220> FEATURE:
<221> NAME/KEY: misc_feature
<222> LOCATION: (8)..(8)
<223> OTHER INFORMATION: n at position 8 is m5c
<220> FEATURE:
<221> NAME/KEY: misc_feature
<222> LOCATION: (13)..(13)
<223> OTHER INFORMATION: n at position 13 is m5c

<400> SEQUENCE: 12
ggngcngngg gtngc                                                    15

<210> SEQ ID NO 13
<211> LENGTH: 48
<212> TYPE: DNA
<213> ORGANISM: Homo sapiens
<220> FEATURE:
<221> NAME/KEY: misc_feature
<222> LOCATION: (4)..(4)
<223> OTHER INFORMATION: n at position 4 is m5c
<220> FEATURE:
<221> NAME/KEY: misc_feature
<222> LOCATION: (7)..(7)
<223> OTHER INFORMATION: n at position 7 is m5c
<220> FEATURE:
<221> NAME/KEY: misc_feature
<222> LOCATION: (10)..(10)
<223> OTHER INFORMATION: n at position 10 is m5c
<220> FEATURE:
<221> NAME/KEY: misc_feature
<222> LOCATION: (15)..(15)
<223> OTHER INFORMATION: n at position 15 is m5c
<220> FEATURE:
<221> NAME/KEY: misc_feature
<222> LOCATION: (36)..(36)
<223> OTHER INFORMATION: n at position 36 is m5c
<220> FEATURE:
<221> NAME/KEY: misc_feature
<222> LOCATION: (39)..(39)
<223> OTHER INFORMATION: n at position 39 is m5c
<220> FEATURE:
<221> NAME/KEY: misc_feature
<222> LOCATION: (41)..(41)
<223> OTHER INFORMATION: n at position 41 is m5c
<220> FEATURE:
<221> NAME/KEY: misc_feature
<222> LOCATION: (46)..(46)
<223> OTHER INFORMATION: n at position 46 is m5c

<400> SEQUENCE: 13
gggnggngcn gggnggggcc ctgatataga gcaggngcng ngggtngc                48

<210> SEQ ID NO 14
<211> LENGTH: 22
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n at position 1 is m5c
<220> FEATURE:
<221> NAME/KEY: misc_feature
<222> LOCATION: (5)..(5)
<223> OTHER INFORMATION: n at position 5 is m5c
<220> FEATURE:
<221> NAME/KEY: misc_feature
<222> LOCATION: (20)..(20)
<223> OTHER INFORMATION: n at position 20 is m5c

<400> SEQUENCE: 14
ngggngggag agggaggggn gg                                            22
```

```
<210> SEQ ID NO 15
<211> LENGTH: 36
<212> TYPE: DNA
<213> ORGANISM: Homo sapiens
<220> FEATURE:
<221> NAME/KEY: misc_feature
<222> LOCATION: (4)..(4)
<223> OTHER INFORMATION: n at position 4 is m5c
<220> FEATURE:
<221> NAME/KEY: misc_feature
<222> LOCATION: (8)..(8)
<223> OTHER INFORMATION: n at position 8 is m5c
<220> FEATURE:
<221> NAME/KEY: misc_feature
<222> LOCATION: (23)..(23)
<223> OTHER INFORMATION: n at position 23 is m5c
<220> FEATURE:
<221> NAME/KEY: misc_feature
<222> LOCATION: (26)..(26)
<223> OTHER INFORMATION: n at position 26 is m5c
<220> FEATURE:
<221> NAME/KEY: misc_feature
<222> LOCATION: (29)..(29)
<223> OTHER INFORMATION: n at position 29 is m5c
<220> FEATURE:
<221> NAME/KEY: misc_feature
<222> LOCATION: (34)..(34)
<223> OTHER INFORMATION: n at position 34 is m5c

<400> SEQUENCE: 15
agcngggngg gagagggagg ggnggngcng gggngg                                36

<210> SEQ ID NO 16
<211> LENGTH: 26
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n at position 6 is m5c
<220> FEATURE:
<221> NAME/KEY: misc_feature
<222> LOCATION: (14)..(14)
<223> OTHER INFORMATION: n at position 14 is m5c
<220> FEATURE:
<221> NAME/KEY: misc_feature
<222> LOCATION: (19)..(19)
<223> OTHER INFORMATION: n at position 19 is m5c

<400> SEQUENCE: 16
gtcccngcag cgcnggctng cgccct                                          26

<210> SEQ ID NO 17
<211> LENGTH: 15
<212> TYPE: DNA
<213> ORGANISM: Homo sapiens
<220> FEATURE:
<221> NAME/KEY: misc_feature
<222> LOCATION: (3)..(3)
<223> OTHER INFORMATION: n at position 3 is m5c
<220> FEATURE:
<221> NAME/KEY: misc_feature
<222> LOCATION: (12)..(12)
<223> OTHER INFORMATION: n at position 12 is m5c

<400> SEQUENCE: 17
gcngcagcca cnggt                                                      15
```

METHYLATED NUCLEOTIDE REGULATION OF GENE EXPRESSION

The invention relates to the field of gene expression, and more particularly to predicting and regulating the expression of the urokinase type plasminogen ("uPA") activator gene.

Aberrant gene expression is frequently observed in cancers. It is believed that improper regulation of certain genes plays a role in the development of many cancers.

Various methods of modulating gene regulation are known in the art. Many involve mutations of sequences important to the transcription or translation of gene products. However, recent evidence suggests that the expression of some genes is regulated by the selective methylation of nucleotides (for example, Holliday, U.S. Pat. No. 5,840,497, and Sheikhnejad, U.S. Pat. No. 5,874,416). Methylation of DNA at the 5 position of the cytosine ("C") in cytosine-guanosine sequences ("CpG") has been implicated in the regulation of gene expression. In particular, some methylated genes appear to be expressed at lower levels than their unmethylated counterparts. (Besterman, et al., *Modern Drug Discovery*, April, 2000, 51-58). Other references of interest include Xing et. al., *Int. J. Cancer*, 81 :443 (1999), and International Publications WO 97/46705 and WO 99/24560.

Following the development of cancer, the role of gene regulation in disease management is less clear. Some cancers appear more prone to metastasize than others. Tumour metastasis is a major factor in long term morbidity and mortality.

Urokinase type plasminogen activator ("uPA") is a protein which may play a role in metastasis. uPA appears to be important to the degradation of components in the extracellular matrix such as laminin, fibronectin and collagen to facilitate the extravasation of tumour cells. uPA has also been implicated in promoting tumour angiogenesis, cell migration and adhesion. Tumour cells that do not express uPA are generally benign or non-metastasizing. Tumour cells that express uPA are in general more aggressive with an increased tendency to metastasize. However, by the time uPA expression is observed in tumour cells, metastasis may have already occurred, reducing the patient's chances for recovery.

Thus, it is an object of the present invention to provide a method for regulation of gene expression, and particularly uPA gene expression.

Surprisingly, specific target nucleotide sequences in the uPA gene have been identified. The invention provides antisense nucleotide sequences corresponding to these target sequences which may be methylated and used to cause a decrease in uPA gene expression. The ability to decrease uPA gene expression is a valuable therapeutic tool in combating tumour metastasis and angiogenesis.

Additionally, regions of the uPA gene have been identified which are useful in predicting the likelihood that a cancer cell population will metastasize. Specifically, the extent of methylation of CpG islands within target sequences in the untranslated region of the uPA gene is predictive of the risk of metastasis. Cells with lower levels of methylation in these target region CpG islands are more likely to metastasize.

Expression of some genes may be regulated by the selective methylation of particular regions within the gene of interest. However, the identification of therapeutically or diagnostically useful target regions for methylation/demethylation of the uPA gene and a means of methylating such regions in vivo has, up to this point, proven elusive.

In one embodiment of the invention there is provided a method for reducing metastasis of tumour cells in a mammalian patient by administering to the patient a methylated antisense oligonucleotide complementary to a target sequence in the uPA gene.

In accordance with the present invention there is provided a method of regulating the expression of a uPA gene in a mammalian cell. The method comprises the steps of: (a) identifying a target nucleotide sequence in the uPA gene; (b) obtaining a methylated antisense deoxy-oligonucleotide sequence substantially complementary to the target sequence, the oligonucleotide sequence having 5 methylated cytosine in place of unmethylated cytosine in the region complementary to the CpG region in the target nucleotide sequence; and (c) exposing the cell to copies of the oligonucleotide sequence under suitable conditions, such that the oligonucleotide sequence enters the nucleus and interacts with the target sequence to promote methylation of the target nucleotide sequence.

In yet another embodiment of the invention there is provided methylated antisense oligonucleotides complementary to a portion of the untranslated region of the uPA gene and containing CpG islands.

In yet another embodiment of the invention there is provided a method of assessing the risk of metastasis of a population of cancer cells in a patient, comprising: (a) amplifying a portion of a uPA target sequence from the cell population; (b) determining the extent of uPA methylation of the target sequence; and (c) comparing the extent of uPA methylation from step (b) with a reference.

FIG. 3 is a depiction of a portion of the untranslated region of the human uPA gene, showing cytosine methylation status in different cell lines as described in Example 8.

Figure 1A:
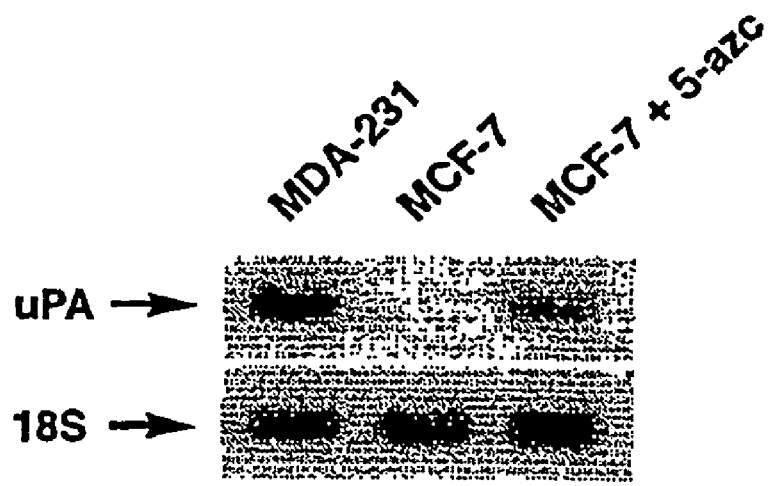
FIG. 1 is a depiction of the results of Example 6 in image and graphical form.

The sequence of the uPA gene is known (Ricco et al., Nucleic Acids Res., 13(8), 2759 (1985) also NCBI Accession No. X02419 (SEQ ID NO: 18)). The transcribed region starts at nucleotide 1227. Nucleotides 1-1226 are the untranscribed region which contains the promoter region. Generalized sites within the uPA promoter region and the first uPA exon which could be methylated have been previously identified. (mt. J. Cancer, 81, 443450, 1999). However, particular methylation sites having regulatory activity have not previously been identified, nor has a method of methylating such sites to reduce uPA expression been proposed.

As used herein, target nucleotide sequences (sometimes referred to as "target sequences") are sequences containing one or more CpG islands, located in the untranslated region of the uPA gene. "CpG islands" are regions of DNA which contain two or more cytosine-guanosine dinucleotide (CpG) sequences with no more than 28 bases between cytosine ("C") residues suitable for 5 methylation. Thus, in light of the disclosure herein, one skilled in the art can identify target sequences in the uPA untranslated region.

As used herein, "designated sequences" are methylated oligonucleotide sequences suitable for interaction with target nucleotide sequences. Preferably, designated sequences having a length of between 15 and 150 bases are used. More preferably, designated sequences having a length of between 15 and 60 bases are used. Yet more preferably, designated sequences having a length of between 15 to 30 bases are used. Examples of designated sequences are shown in Table 1. However, it will be apparent to those skilled in the art, in light of the disclosure herein, that other designated sequences are contemplated and can be readily synthesized according to standard procedures.

Preferably, deoxynucleotides methylated oligonucleotide sequences substantially complementary to a portion of the uPA promoter region within the uPA untranslated region and containing CpG islands are used. In some instances it will be desirable to use methylated oligonucleotides substantially complementary to SEQ ID NOS: 5-17, more preferably SEQ ID NOS:6, 7, 10, 11, and 13-16, yet more preferably SEQ ID NOS:7 and 15. In some cases it will be desirable to use methylated oligonucleotides complementary to a portion of the untranslated region of the uPA gene including the sequences 5'GGCGG (SEQ ID NO:19).

As used herein, "reducing sequences" are designated sequences which-are effective in reducing uPA gene expression in at least one cell line.

As used herein, "impeding sequences" are designated sequences which are effective to significantly impede the ability of highly invasive tumour cells to invade through MATRIGEL™.

The selective methylation of target nucleotide sequences can be readily carried out using the method herein disclosed of methylating target nucleotide sequences wherein cells containing a target nucleotide sequence are exposed to substantially complementary methylated oligonucleotides under conditions which permit interaction between the methylated oligonucleotides and the target nucleotide sequence in the nucleus of the cell.

An oligonucleotide is substantially complementary to a target sequence if the bases of the two sequences are complementary (C corresponding to G and A to T) for at least 75% of the oligonucleotide's length, CpG islands in the target sequence are exactly complementary in base sequence (but not necessarily methylation) to the corresponding portion of the oligonucleotide, and the oligonucleotide is capable of forming a stable complex with the target sequence in the cell.

Table 1 lists some target sequences complementary to corresponding designated sequences. Where a target sequence contains 5 methyl cytosine Immediately 5' to G, the designated sequence preferably includes 5 methyl cytosine as the complementary nucleotide to the G, such that the complementary sequence to 5' CmG 3' would be 5' CmG3'. (For example, the designated sequence complementary to SEQ. ID. No. 1 is CCmGGGCTTATTGCTTTCmG).

Preferably, methylated antisense oligonucleotide sequences contain two or more methylated cytosines with no more than 28 bases between 5 methyl cytosine residues in the region complementary to the CpG region in the target nucleotide sequence.

It will be readily understood that nucleotide analogues may be used to replace some or all of the nucleotides in a designated sequence in appropriate circumstances, although C and G in CpG regions are preferably not replaced by analogues. Thus, substantially complementary oligonucleotides may have some or all nucleotide monomers replaced by suitable analogues In particular, analogues such as phosphothioates, methyl phosphonates or P-ethoxyphosphanates may offer advantages in some circumstances. Such nucleotides are generally resistant to nucleases and may therefore provide greater oligonucleotide stability. Methyl phosphonates and P-ethoxyphosphonates may be incorporated into liposomes with high efficiency and are less prone to activate RNaseH or complement than native nucleotides. In light of the disclosure herein and known standard techniques, it is within the capacity of one skilled in the art to produce and identify suitable oligonucleotide sequences containing analogues.

Methylated antisense nucleotides may be of any length which permits effective uptake into cancer cells, interaction of the oligonucleotide with its corresponding target sequence and methylation of cytosine in the target sequence. The exact length of the antisense methylated oligonucleotide is not critical so long as a stable complex is formed between the target sequence (sense strand) and the antisense methylated oligonucleotide. Methylated oligonucleotide sequences are preferably between about 15 and 60 nucleotides long, more preferably between about 15 to 30 nucleotides long. (Matsuno et al., Methods in Enzymology, Vol. 313, pg. 359)

Without limiting the invention to any particular mechanism of action, the mechanism probably relates to binding of the antisense sequence to the target nucleotide sequence thereby providing the DNA methyltransferase (Mtase) enzyme with a hemimethylated substrate, allowing DNA Mtase to methylate complementary GC sites using methylated antisense strand as the template.

Methods of synthesizing DNA oligonucleotide sequences having 5 methylated cytosine in place of unmethylated cytosine and complementary to a CpG island in a particular nucleotide sequence are known in the art and, if desired, such oligonucleotides may be ordered commercially or synthesized according to standard methods. Similarly, techniques for the synthesis and purification of oligonucleotides combining natural nucleotides with analogue monomers are known in the art.

Methods of exposing mammalian cells to oligonucleotides under conditions suitable for the uptake of oligonucleotides into the nucleus whereby DNA is transfected into cells (for example, by using agents like LIPOFECTIN™) are known in the art. Where the term "suitable conditions" is used herein, this means conditions which permit the uptake of a particular designated sequences into the nucleus of the cell in a form which permits interaction between the designated sequence and the target sequence resulting in the 5 methylation of cytosine in the target sequence sufficient to reduce its expression. A person skilled in the art, in light of the disclosure contained herein, could identify "suitable conditions" in respect of particular oligonucleotides.

All suitable methods of delivery of antisense nucleotides known in the art can be utilized for this invention. Nonetheless, liposomes are particularly contemplated. Cationic lipids (also called cytofectins) are a known delivery vehicle, and may be suitable in some situations. (Sean et al., *In Methods Enzymol* (2000), 313 (Part A) pg 322-341).

Another useful method for oligonucleotide delivery is coupling the oligonucleotide to a relatively small molecule that can enhance its entry into cells. Dendrimers, umbrella amphiphiles, transport enhancing proteins and ligand-linker-antisense conjugates can each be combined with the methylated complementary oligonucleotides of the present invention to permit oligonucleotide delivery. (*In Methods Enzymol* (2000), 313 (Part A) pg. 297-321; also Hughes et al., *In Methods Enzymol* (2000), 313 (Part A) pg. 342-358). One skilled in the art, in light of the disclosure herein, can readily select from any available delivery technology with reference to the oligonucleotide to be delivered, the cell type to be treated, the patients condition and other factors including toxicity and interactions with plasma.

Other methods of introducing designated sequences into cells will be apparent to those skilled in the art, in light of the disclosure herein. For example, transfection by infection of mammalian cells by a viral vector containing the methylated antisense oligos of the present invention is also contemplated by the invention as a method for delivering the DNA into the mammalian cells. Similarly, a viral vector may be used to permit treatment of cells within a subject by infection of the mammalian subject. Subjects may also receive designated sequences by injection, such as i.v. or i.p. or intramuscular injection of designated sequences in a pharmaceutically acceptable carrier. Injection directly into the tumour site will be preferred in some circumstances. Treatment can be repeated at scheduled intervals.

Preferably several treatments are performed over a 1-4 week period following which methylation of the uPA utr in cancer cells from the patient is determined and compared to a standard, substantially according to the diagnostic method of the present invention. Where the patient's cancer cells show significant demethylation of the uPA utr relative to normal, non-malignant cells from a similar source, treatments should be continued at least until methylation reaches normal levels. In some cases it will also be desirable to administer designated sequences on an ongoing basis to reduce the likelihood of significant demethylation developing.

Thus, in light of the disclosure herein, it is within the capacity of one skilled in the art to introduce a designated sequence into cells having a uPA gene causing methylation of the target sequence and reduced uPA expression.

A diagnostic test for assessing the degree of malignancy of a cancer either from a biopsy or more preferably from a biological fluid or mucosa of the patient is also provided. Diagnostic tools requiring less invasive techniques are valuable in reducing patient discomfort and may also reduce the cost of diagnosis. It is useful to have a method to categorize the aggressiveness of a cancer at an early stage as this assists in selecting a suitable therapy and/or life planning.

In one embodiment of the diagnostic method, a portion of the untranslated region ("utr") of the uPA gene from a cell population of interest is examined and its methylation status is determined. Methylation status may be assessed by any suitable means, including the use of methylation-sensitive restriction enzymes and methylation specific polymerase chain reaction ("msPCR"). Conveniently, msPCR is used to selectively amplify the untranslated region of the uPA gene. The PCR amplification products can then be analyzed using conventional means to determine the methylation status of the uPA utr. Cells having comparatively low levels of methylation of the uPA utr, and particularly the promoter region therein, indicate a significant risk of metastasis.

Methylation status may be graded according to any appropriate method. For example, methylation status of a particular uPA gene region may be compared to normal, non-malignant tissue from the same or a similar source as the sample. Samples having less methylation than the normal reference are considered to present a metastasis risk. In some instances, samples may also be compared to cells derived from the same or similar tissue source and known to be highly invasive (such as cell lines having defined characteristics). A sample having a methylation status closely resembling the methylation status of the highly invasive cells, is assessed as presenting a greater risk of metastasis than a sample having a greater extent of methylation.

For example, when examining breast cancer cells, a suitable 'normal' reference would be normal mammary epithelial cells from a healthy subject of a similar age and ethnicity to the patient . A suitable reference for highly invasive cells would be MDA-231 cells. The diagnostic method may be applied to any cancer presenting a risk of uPA related metastasis. The diagnostic method is especially suited for use with breast cancer, prostate cancer, lung cancer and colon cancer.

Methods for conducting msPCR are known in the art, and can be readily applied to amplify the uPA utr in light of the disclosure herein. [See for example Herman, et al., PNAS 93:9821(1996)].

The region amplified by msPCR preferably includes at least a portion of the uPA untranslated region containing one or more CpG islands. In some cases it is desirable to amplify a region including at least a portion of the uPA promoter containing CpG islands. Still more preferably, the region amplified includes uPA base pairs 592 to 891. In some cases it will be desirable to amplify a portion of the untranslated region of the uPA gene including the sequence 5'GGCGG. In one embodiment of the diagnostic method of the present invention the uPA region amplified contains a nucleotide sequence identical or substantially homologous to one of SEQ. ID. NOs. 5 to 17, preferably one of SEQ. ID. NOs. 7, 9,14, 15, 16 and 17, even more preferably one of SEQ. ID. NOs. 7, 9 and 15. msPCR primers are complementary to a portion of the uPA gene, and preferably to a portion of the uPA utr. Even more preferably, the region of the uPA gene to which the primer is complementary is within 20 nucleotides of a CpG island. Factors to be considered in the selection of PCR primers are known and a person skilled in the art could prepare suitable primers, in light of the disclosure herein.

The invention provides a process of assessing the risk of metastasis presented by a population of mammalian cancer cells having a functional uPA gene, comprising: (a) determining the extent of cytosine methylation in a portion of the uPA gene 5' untranslated region containing a CpG island; and (b) comparing the extent of methylation from (a) to a reference.

As a therapy, the methylated oligonucleotide method of the present invention is distinguished from and offers significant advantages over conventional antisense compositions which are believed to act to inhibit translation of mRNA, but not transcription of the gene to produce mRNA. Promoter-specific methylated oligonuclotides of the present invention may inhibit gene activity at the transcriptional level so that cells cannot escape inhibition by recycling their mRNA. Methylation imprinting in a select region of the promoter or untranscribed region may silence the uPA gene in a heritable manner, inhibiting cellular recycling which might otherwise reduce the inhibitory effects of oligonucleotides.

Thus, the present invention reduces the need for the continuous delivery of large amounts of chemically-modified antisense agents.

EXAMPLES

Example 1

Human tumour cells expressing high levels of uPA are selected. Suitable cell lines include PC-3 and MDA-MB-231 cell lines.

The selected cells are treated with graded doses of certain selected designated sequences. The optimal dosage level is determined empirically. The dosage level is preferably in the range of 0.5 to 30 micrograms per ml, more preferably in the range from 1 to 15 micrograms per ml, and even more preferably in the range of 5 to 10 micrograms per ml.

A control population of tumour cells is treated with either PBS (phosphate buffered saline) or non-specific oligonucleotides having a similar length to the designated sequences employed but having no change of cytosine to methyl cytosine.

The tumour cells are incubated under suitable conditions with the oligonucleotides for between 6 and 48 hours. The exact period of incubation can be determined empirically in light of the sequence characteristics and the disclosure contained herein, by a person skilled in the art.

After incubation of the tumour cells with the oligonucleotides, cellular RNA is extracted and evaluated for uPA mRNA using northern blot analysis, according to methods known in the art. Expression of actin, cyclophiline or 18S RNA is used as a control for the quantification of the uPA expression. Tumour cell lines treated with designated sequences show a statistically significant reduction of uPA gene expression. Some designated sequences reduce uPA gene expression in some cell lines but not others.

Thus, in light of the disclosure contained herein, it is within the capacity of a person skilled in the art to screen methylated oligonucleotides for effectiveness in reducing the expression of uPA in specific cell lines. Designated sequences which are effective in reducing uPA expression in at least one cell line are "reducing" sequences.

Example 2

The ability of designated sequences to impede the passage of tumour cells through MATRIGEL™ (a measure of metastatic potential of cells) is evaluated using a two compartment Boyden chamber invasion assay according to procedures known in the art. (Albini, A. et al., *Chemical Research*, 47:3239-3245, 1987).

Highly invasive tumour cells are placed in a compartment of a Boyden chamber. The impact of incubation of the highly invasive tumour cells with reducing sequences on the ability of the highly invasive tumour cells to invade through the MATRIGEL™ is assessed by incubating one cell population in the presence of reducing sequences under suitable conditions and comparing this population to a population not exposed to reducing sequences. Those designated sequences which significantly impede the ability of highly invasive tumour cells to invade through MATRIGEL™ are of particular interest. These are "impeding sequences".

Example 3

The ability of methylated oligonucleotides to reduce uPA expression by tumour cells in vivo is assessed according to standard procedures for assessing gene expression. (For example Xing, R. et al., *Cancer Research*, 57:3585-3593, 1997).

1,000,000 uPA expressing cells are inoculated into the mammary fat pads of 4-6 week old female/C/nu/nu mice. The animals are then injected interperitoneally (i.p.) with either PBS, non-specific oligonucleotides or impeding sequences. This i.p. treatment is repeated every week for 7-8 weeks and the animals are monitored regularly and the tumour volume is determined.

A statistically significant reduction in the rate of tumour growth observed between animals receiving impeding sequences and other animals indicates that the impeding sequences are advantageous in reducing tumour growth.

At the end of the study, all animals are sacrificed and evaluated for the presence of macroscopic and microscopic tumour metastasis in the lungs and lymph nodes. Statistically significant reduction in macroscopic and microscopic metastasises are observed between animals treated with impeding sequences and control animals.

Example 4

Animals are innoculated with uPA expressing cells as in Example 3. However, tumours are allowed to grow in animals to palpable or measurable (2-50 mm square) stage before initiating treatment with oligonucleotides. Tumour growth is assessed. This example is conducted according to procedures known in the art, and in light of the disclosure contained herein. Statistically significant differences observed between the animals treated with impeding sequences and other animals demonstrate the efficacy of impeding sequences in reversing or slowing cancer progression.

Thus, it will be apparent that there has been provided a method for methylated nucleotide regulation of gene expression.

Example 5

Tumour cells are collected from either a tumour biopsy or blood, urine or mucosa of human cancer patients. Methylation specific PCR is used to amplify the DNA of the uPA promoter region. (uPA is minimally expressed in non-tumour cells so these do not significantly interfere.) DNA sequence analysis is performed to measure the extent and the change in the methylation status of the uPA gene. The methylation status of the tumour cells is compared to the methylation status of the comparable DNA region of control cells of varying metastatic aggressiveness. Aggressive cell types are found to have lower levels of methylation of the uPA promoter region than normal cells. uPA promoter region demethylation can be correlated with an increased risk to metastasis in human cancer patients.

Example 6

Figure 1B:
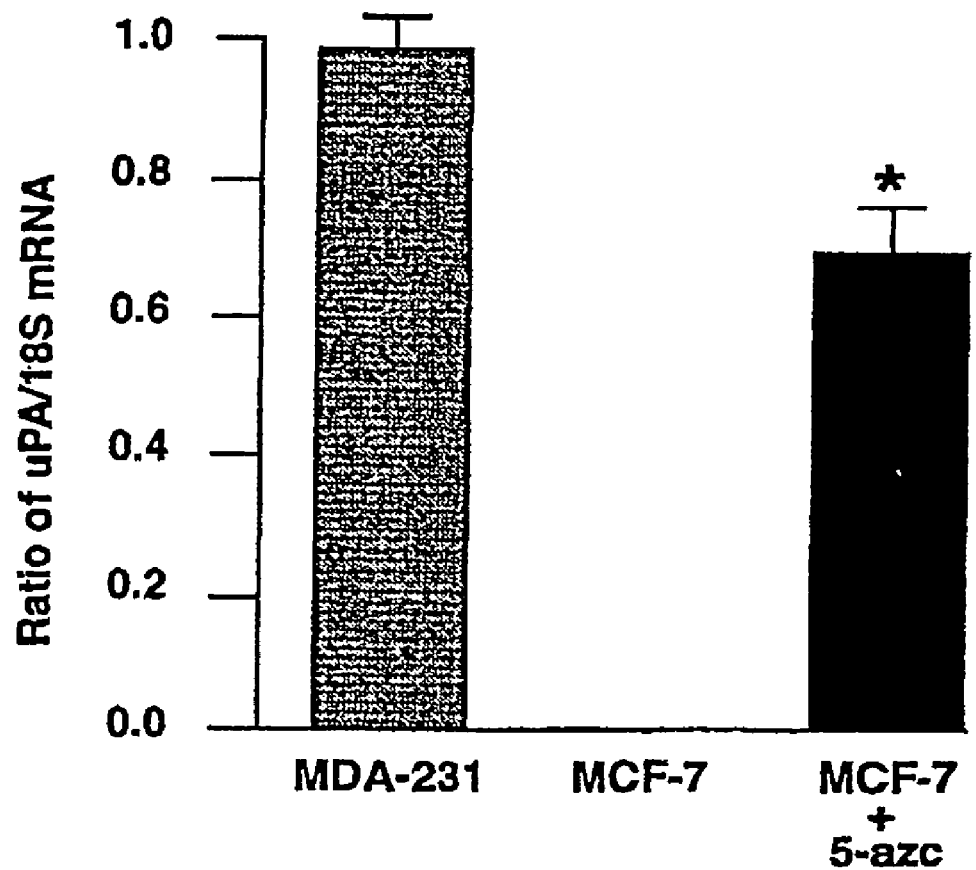

Human breast cancer cells MCF-7 were maintained in culture and at 65% confluent cells were treated with vehicle alone (MCF-7) or 25 uM of the demethylating agent 5 azc (MCF-7+5azc) for ten days. MDA-231 cells were used as positive control (MDA-231) for uPA expression. At the end of this period 20 μg of cellular RNA from each group were electophoresed on a 1.1% agarose/formaldehyde gel and human uPA cDNA or with a $^{32}p$ labeled 18 S RNA probe. The results are shown in FIG. 1. All blots (FIG. 1A) were quantified by densitometric scanning (FIG. 1B). Significant difference from control cells is represented by an asterisk ($p<0.05$).

Treatment of MCF-7 cells which fail to express significant levels of uPA with methylation inhibitor 5-azc results in marked induction of uPA mRNA as seen by Northern blot analysis.

Example 7

Experimenting with 2 different treatment doses, human breast cancer cells MDA-231 were transfected with one of: methylated antisense oligonucleotide complementary to SEQ. ID. NO. 15 (mAS); the oligonucleotide of SEQ. ID. NO. 15 (mS); or unmethylated antisense oligonucleotide complementary to SEQ. ID. NO. 15 (AS). Transfection was allowed to proceed for 18 hours using LIPFECTAMIN™ (GIBCO™) according to manufacturer's instructions. At the end of this treatment, 20 micrograms of cellular RNA from each treatment group was obtained according to standard methods and was electrophoresed on a 1.1% agarose/formaldehyde gel and blotted to a nylon membrane by capillary action. Blots were hybridized with a $^{32}$P labeled human uPA cDNA or with a $^{32}$P labeled 18 S RNA probe. The ratio of uPA expression to 18 S mRNA expression was calculated.

Figure 2A:
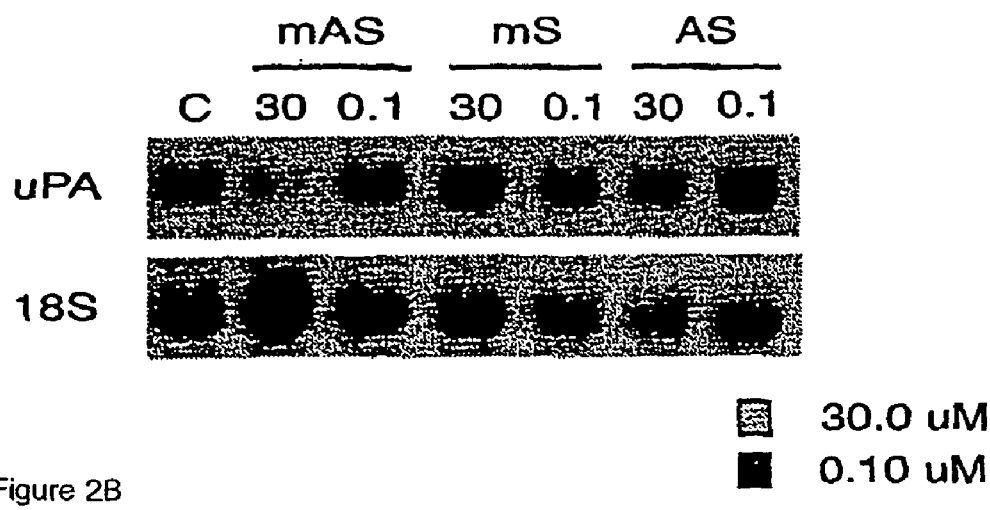
FIG. 2 is a depiction of the results of Example 7 in image and graphical form.
Figure 2B:
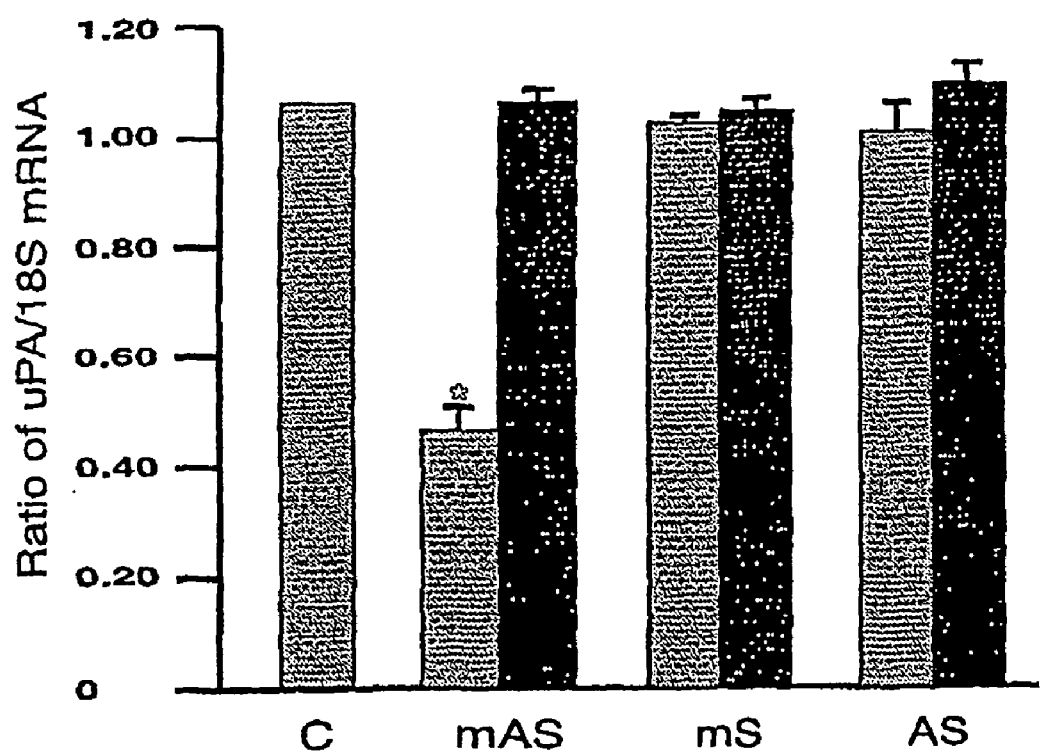

The results of this example are depicted in FIG. 2. All blots (FIG. 2A) were quantified by densitometric scanning (FIG. 2B). Significant difference from control cells is represented by asterisks (p<0.05). Treatment of MD-231 cells with 30 micromolar mAS resulted in significant inhibition of uPA mRNA expression as compared to control groups of cells treated with mS or AS oligonucleotides under similar experimental conditions as seen by Northern blot analysis.

Example 8

Determination of methylation status of uPA gene promoter in human breast cancer cells and human prostate cancer cells.

Total cellular genomic DNA was extracted from MDA-231, LNCap and MCF-7 cells. 2 micrograms of genomic DNA was treated with sodium bisulfite at 55° C. for 14 hours which results in all unmethylated cystosines (C) being converted to uracil (U). During subsequent amplification, these uracils are further converted to Thymidine (T) via amplification using nested PCR using uPA primers corresponding to 5'UTR 572-591 bp (caggtgcatgggaggaagca) and 892-911 bp (gagtgccgcggtcctgagat) of uPA. This allows ready detection of the level of cytosine methylation in the sample.

As depicted in FIG. 3, which provides a comparative view of a portion of the uPA utr across cell types, greater than 90% of cytosines are methylated within the CpG islands of the uPA promoter in MCF-7 cells (line 4). The top line of FIG. 3 shows the unmodified sequence of part of the untranslated region of the uPA gene. In contrast, MD-231 cells which exhibit high uPA levels contain unmethylated cytosine (line 5). Thus, methylation status of the uPA utr is predictive of uPA expression and the risk of metastasis.

TABLE 1

| SEQ ID NO. | |
|---|---|
| 1 | CmGAAAGCA ATAAGCCCmGG |
| 2 | TGTCm GCmGTGATGAA GACTTCACAG CTCCATCCAG CmGACC |
| 3 | Cm GCmGTGATGAA GACTTCACAG CTCCATCCAG CmG |
| 4 | CmGGGGACTCCTTGCACTGGG GCAGGCCCCmG |
| 5 | ACmG CTGTTGGGTC CCCTCCmGCTG GAGATCmGCmGC |
| 6 | AG CmGTTGCmGGAA GCACGCmGGGG TC |
| 7 | GCCmGG GCmGGGGAGAGG GAGGGGCmGGC GCCmGGGGCmGGG |
| 8 | GGCmG CCmGCmGGGTCmG CAGCACAGTC GGAGACCmGCA GCCmGGAGCC CmGGG |
| 9 | CmGCTG GAGATCmGCmGC TTCCCCCAAA TCTTTGTGAG CmGTTGCmGGAA GCACmGCmGGGG TCCmGGGTCmGC TGAGCmGCTGC AAGACAGGGG AGGGAGCCmGG G CmGGGAGAGG GAGGGGCmGGC GCCmGGGGCmGG GCCCTGATAT AGAGCAGGCmG CCmGCmGGGTCmG C |
| 10 | CmGCmGGGG TCCmGGGTCmGC TGA |
| 11 | GGGCmGGCm GCCmGGGGCm GGG |
| 12 | GGCmG CCmGCmGGGTCmG C |
| 13 | GGGCmGGCm GCCmGGGGCmGG GCCCTGATAT AGAGCAGGCmG CCmGCmGGGTCmG C |
| 14 | CmG G GCmGGGAGAGG GAGGGGCmGG |
| 15 | AGCCmGGGCmGGGGAGAGGGAGGGGCmG GCmGCCmGGGGCmGG |
| 16 | GTC CCCmGCAGCGC CmGGCTCmGCGC CCT |
| 17 | GCCmG CAGCCACCmGG T |

We claim:

1. An oligonucleotide that is from 15 to 150 nucleotides in length wherein said oligonucleotide comprises a nucleic acid sequence that is exactly complementary to at least one CpG island present in a portion of a nucleic acid molecule having a nucleotide sequence of nucleotide position 1 to nucleotide position 1226 of SEQ ID NO: 18, and wherein said oligonucleotide: (i) forms a stable complex in a mammalian cell with said portion of said nucleic acid molecule; and (ii) comprises one or more 5-methylated cytosines complementary to a guanosine of said CpG island.

2. The oligonucleotide of claim 1 wherein the oligonucleotide is exactly complementary to said portion.

3. The oligonucleotide of claim 1 that is from 15 to 60 nucleotides in length.

4. The oligonucleotide of claim 1 that is from 15 to 30 nucleotides in length.

5. The oligonucleotide of claim 1 wherein said portion comprises a promoter region.

6. The oligonucleotide of claim 1 wherein said portion comprises the nucleotide sequence of SEQ ID NO:7.

7. The oligonucleotide of claim 1 wherein said portion comprises the nucleotide sequence of SEQ ID NO: 19.

8. The oligonucleotide of claim 1 wherein said oligonucleotide comprises one or more nucleotide analogues.

9. The oligonucleotide of claim 8 wherein said nucleotide analogues are phosphathioates, methyl phosphonates, or P-ethoxyphosphonates.

10. A method of amplifying at least a portion of a nucleotide molecule having a nucleotide sequence of nucleotide position 1 to nucleotide position 1226 of SEQ ID NO:18, said method comprising:
   (a) contacting a pair of primers with a DNA sample, wherein the primers specifically hybridize to nucleotide sequences that flank at least one CpG island of nucleotide position 1 to nucleotide position 1226 of SEQ ID NO:18; and
   (b) amplifying at least a portion of the nucleotide molecule by methylation sensitive amplification.

11. The method of claim 10 wherein said primers are methylation sensitive primers.

12. The method of claim 10 wherein said portion comprises nucleic acid sequence of nucleotide position 592 to 891 of SEQ ID NO: 18.

13. The method of claim 10 wherein said portion comprises nucleotide sequence of SEQ ID NO:7.

14. The method of claim 10 wherein said portion comprises the nucleotide sequence of SEQ ID NO: 19.

15. The method of claim 10 wherein said portion is amplified using primers that are within 20 nucleotides of a CpG island.

16. An isolated cell comprising an oligonucleotide that is from 15 to 150 nucleotides in length wherein said oligonucleotide comprises a nucleic acid sequence that is exactly complementary to at least one CpG island in a portion of a nucleic acid molecule having a nucleotide sequence of nucleotide position 1 to nucleotide position 1226 of SEQ ID NO: 18, and wherein said oligonucleotide; (i) forms a stable complex in a mammalian cell with said portion of said nucleic acid molecule; and (ii) comprises one or more 5-methylated cytosines complementary to a guanosine of said CpG island.

17. A kit comprising the oligonucleotide of claim 1.

18. The kit of claim 17 wherein the oligonucleotide is exactly complementary to said portion.

19. The kit of claim 17, wherein said portion comprises nucleic acid sequence of nucleotide position 592 to 891 of SEQ ID NO: 18.

20. The kit of claim 17 wherein said portion comprises nucleotide sequence of SEQ ID NO:7.

21. The kit of claim 17 wherein said portion comprises the nucleotide sequence of SEQ ID NO:19.

22. The isolated cell of claim 16 wherein the oligonucleotide is exactly complementary to said portion.

* * * * *